May 7, 1940. M. H. HORVATH Plant Pat. 385
ROSE
Filed Dec. 7, 1939
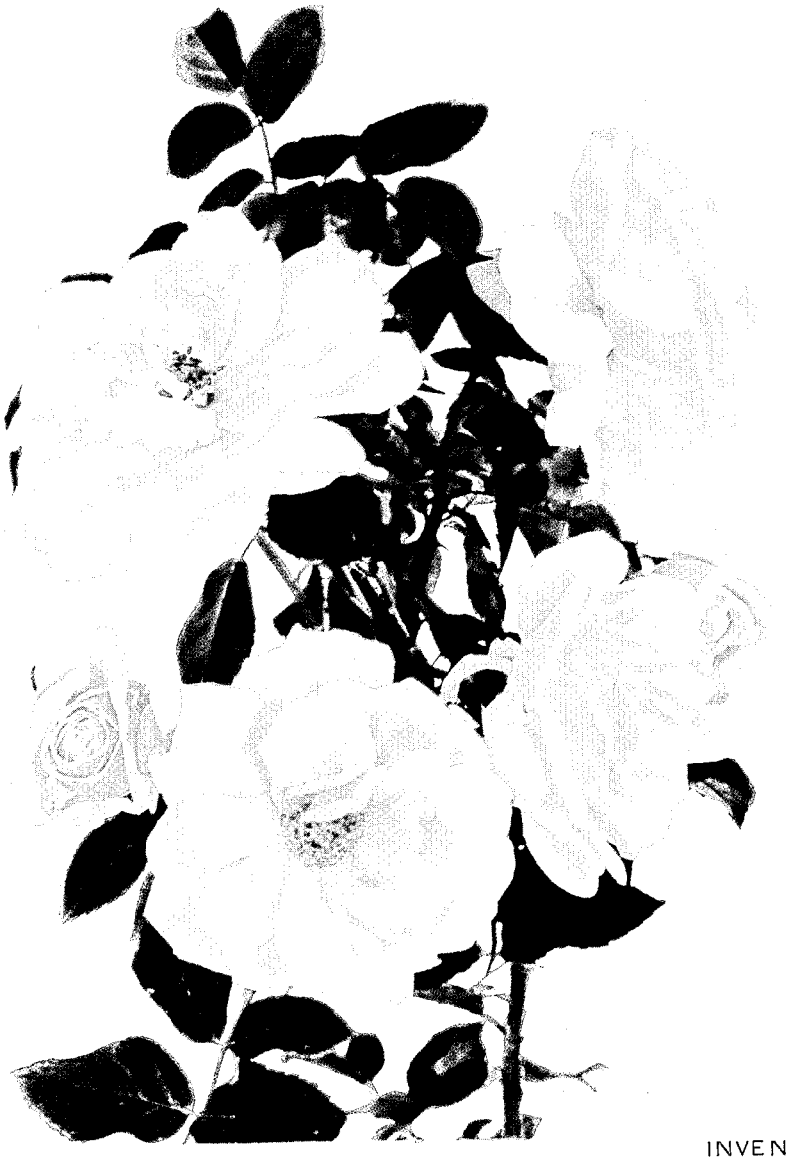
INVENTOR
MICHAEL H. HORVATH
BY John A. Bernard
HIS ATTORNEY Patented May 7, 1940

UNITED STATES PATENT OFFICE

385

ROSE

Michael H. Horvath, Mentor, Ohio

Application December 7, 1939, Serial No. 308,038

1 Claim. (Cl. 47—61)

This invention relates to a new variety of rose, a *Rosa setigera* hybrid.

The variety was originally produced by crossing a variety Doubloons, as the female or seed parent, with a variety Clio, a Damascena Hybrid, as the male or pollen parent, and it has been asexually reproduced true to form in considerable quantity.

The variety is exceptionally hardy and disease resistant, and, unprotected, has survived without damage a severe winter season during which the temperature was as low as thirty degrees below zero Fahrenheit for an appreciable period. It has been grown unprotected in the northeastern and north middle western parts of the United States and appears to be adapted for growth, unprotected, generally throughout the United States and elsewhere throughout regions in the temperate zone. It can be grown protected in colder regions where the growing of roses has been difficult.

The plant is a strong climber attaining a height of seven to ten feet.

The leaves are abundant, large, shiny, closely set and glabrous and, on the upper surface, are medium green with a slight reddish shade, comparable to Maerz & Paul Plate No. 31–A–12. The leaves are very resistant to mildew.

The flowers are large, abundant, and semi-globular or cup-shaped in form. They are borne on spur branches, mostly in groups of threes, on terminals of the main stock and terminals of strong laterals, beginning generally at one and one-half to two feet from the base of the plant and being irregularly distributed upwardly therefrom entirely to the top of the plant. The pedicels are from two to three inches long, stiff, generally upright, and well proportioned to the flowers so that they support the flowers without bending.

The color of the flowers shades from a coral pink, comparable to Maerz & Paul Plate No. 2–F–9, particularly in the early stage of blooming, to white with a a pink cast, comparable to Maerz & Paul Plate No. 1–B–1, and light pink, comparable to Maerz & Paul Plate No. 1–E–1. In all stages of blooming, the flowers have a silvery reflex color or sheen, and a yellow ochre center, comparable to Maerz & Paul Plate No. 11–L–7.

Each flower has from thirty-five to forty petals which are imbricated and extend generally upwardly and outwardly. They are generally deeply concave upwardly near their base, becoming progressively less concave toward their margins, and have downwardly and outwardly, gradually and smoothly recurving margins.

The variety is characteristically a persistent grower and bloomer, though not a recurrent bloomer, the flowers being abundant throughout the blooming period which begins in June and last four to five weeks. Throughout the blooming period the flowers are consistent in quantity and quality.

The blooms and plant are excellent for cutting and the flowers have good lasting qualities both as to physical condition and color, whether cut or uncut.

The plant is distinguished principally by the prolificacy of blooms, the beauty and stability of the rare and delicate coloring of the flowers, the beauty of the shape of the flowers, the above-average persistence of the petals, the exceptional hardiness of the plant, and its above-average resistance to disease.

The following tabulation is a detailed description of the new variety.

*General*

Parentage:
- *Seedling — seed parent.* — "Doubloons," a *setigera* hybrid. *Pollen parent.*—"Clio," a Damascena hybrid.

Classification:
- *Botanic.*—*Setigera* hybrid.

*Flower*

Blooming habit:
- *Location where observations were made.*—Trial field of Michael H. Horvath, Mentor, Ohio.
- *Flowering.*—June to early July (northern Ohio), continuously throughout period.

Bud:
- *Size.*—Large.
- *Form.*—Semi-globular.
- *Color.*—When sepals first divide—reddish or deep pink, comparable to Maerz & Paul Plate No. 1–I–7. When petals begin to unfurl—yellow undertone and blush pink shading, comparable to Maerz & Paul Plate No. 2–F–9. When half blown—yellow undertone and blush pink shading comparable to Récamier, Maerz & Paul Plate No. 1–G–8.
- *Sepals.*—Regular, rather large and smooth.
- *Calyx.*—Shape—normal, light green with reddish cast. Size—average or medium. Aspect — normal with semi-pubescence. Aroma when rubbed—slight damascenal scent.

*Peduncle.*—Length—about twelve inches. Aspect—some rounded and some flattened on two sides, with slight prickles. Color—light green. Strength—ample, well proportioned to bloom and holds flowers generally upright without pendancy. Opening—opens well in blooming season regardless of weather conditions.

Bloom:

*Size.*—Large, three and one-half to four and one-half inches in diameter.

*Borne.*—Mostly in threes on terminals of main stalk and of strong laterals.

*Stems.*—Stiff, medium and generally upright.

*Form.*—When first opened, saucer shaped.

*Permanence.*—Good until ready to shed.

Petalage: Number of petals under normal conditions, thirty-five to forty.

*Color.*—Center of flower—shades from white with a pink cast, Maerz & Paul Plate No. 1–B–1, to a light pink, Maerz & Paul Plate No. 2–F–9, all having a silvery reflex color. Outer petals—same. Base of petals—same. Inside of petals—same. Reverse of petals—same. General tonality from a distance—light pink comparable to Maerz & Paul Plate No. 1–B–1, with a silvery reflex color or sheen.

*Variegations.*—None.

*Discoloration.*—General tonality remains constant from first day until the end.

Petals:

*Texture.*—Medium thickness.

*Form.*—Shell shaped, concave upwardly with recurvant margins.

*Arrangement.*—Imbricated.

*Petaloids in center.*—Few.

*Persistence.*—On bloom—above average.

*Fragrance.*—Damascenal.

*Nature.*—Slight.

*Lasting quality.*—On plant—very good; as a cut flower—very good.

Genital organs:

*Stamens.*—Normal in quantity and size and of medium length.

*Color.*—Yellow.

*Arrangement.*—Normal and regular.

*Pollen.*—Yellow.

*Styles.*—Light green with reddish prickles, medium to normal in size, shape, and arrangement.

*Stigmas.*—Light yellow and of average size and shape.

*Ovaries.*—Semi-globular and somewhat depressed.

Fruit:

*Form.*—Semi-globular and rather depressed, medium in size.

*Aspect.*—Smooth.

*Color at maturity.*—Yellow with red shading.

*Sepals.*—Average.

*Plant*

Form: A climber.

Growth: Strong, to a height of 8 to 10 feet with average spread.

Foliage: Closely set and glabrous with seven leaflets.

*Size.*—Medium.

*Quantity.*—Ample.

*Color.*—New foliage: upper side—medium green with reddish shade, comparable to Maerz & Paul Plate No. 31–A–12; under side—light green. Old foliage: upper side—medium green with reddish shade; under side—light green.

*Shape.*—Normal, somewhat ovate with short points.

*Texture.*—Upper side—smooth; under side—smooth. Ribs and veins—same color, and normal and average.

*Edges.*—Serrated, serrations small, regular.

*Rachis.*—Smooth on the upper surface with straight prickles on the lower surface. Color: under side—light green; upper side—light green.

*Stipules.*—Normal in size and surface with regular arrangement.

*Disease resistance.*—Above average, exceptionally resistant to mildew.

Wood:

*New wood.*—Color—light green. Bark—light green, smooth.

*Old wood.*—Color—light green with bronze cast. Bark—rough and very thorny with close and abundant thorns.

Thorns:

*Quantity on main stalks from base.*—Very abundant.

*On laterals from stalk.*—Very abundant.

*Form.*—Generally straight and very sharply pointed, and extend generally outwardly from stalk.

*Color.*—When young—reddish. When old—yellowish, turning gray with age.

*Position.*—Irregularly distributed over all the stalks but less on laterals than on main stalk.

*Prickles.*—Very few.

*Short needles.*—Few.

Having now fully shown and described my new variety of rose and the mode of its production, what I claim and desire to secure by Letters Patent of the United States is:

A variety of hybrid rose as herein shown and described, and characterized particularly by vigourous growth, extreme hardiness, and resistance to disease, prolificacy of blooms of very large flowers of superior beauty in shape and color with petals of a very distinctive pink and having a silvery reflex color or sheen, consistency of blooming throughout the blooming period, and the persistence of petals and stability of the color, in cut and uncut condition.

MICHAEL H. HORVATH.